United States Patent [19]

Sirota

[11] Patent Number: 4,898,179

[45] Date of Patent: Feb. 6, 1990

[54] DEVICE FOR DETECTING, MONITORING, DISPLAYING AND RECORDING OF MATERIAL AND FETAL VITAL SIGNS AND PERMITTING COMMUNICATION BETWEEN A WOMAN AND HER FETUS

[76] Inventor: Vladimir Sirota, 2111 Jefferson Davis Hwy., Apt. 803 South, Arlington, Va. 22202

[21] Appl. No.: 223,011

[22] Filed: Jul. 22, 1988

Related U.S. Application Data

[63] Continuation-in-part of Ser. No. 60,812, Jun. 12, 1987, abandoned, which is a continuation-in-part of Ser. No. 745,684, Jun. 17, 1985, Pat. No. 4,672,975.

[51] Int. Cl.⁴ ................................................ A61B 5/02
[52] U.S. Cl. .................................... 128/670; 128/698; 128/700; 128/706; 128/710; 128/715; 128/782; 381/67
[58] Field of Search .................... 128/669.03, 689, 698, 128/715, 773, 775, 782, 897; 381/67, 124; 446/303, 472

[56] References Cited

U.S. PATENT DOCUMENTS

| 3,348,535 | 10/1967 | Gregg | 128/715 |
|---|---|---|---|
| 3,811,428 | 5/1974 | Van Horn et al. | 128/698 |
| 3,916,878 | 11/1975 | Courtin et al. | 128/698 |
| 4,601,668 | 7/1986 | Sirota | 446/472 |
| 4,740,186 | 4/1988 | Sirota | 446/303 |

FOREIGN PATENT DOCUMENTS

| 1445220 | 5/1966 | France | 128/698 |
|---|---|---|---|
| 2115934 | 9/1983 | United Kingdom | 128/715 |

Primary Examiner—William E. Kamm
Attorney, Agent, or Firm—Jerry T. Kearns

[57] ABSTRACT

A device for detecting, monitoring, displaying and recording a representation of the heartbeats of a pregnant woman and her fetus. The heartbeat of each is monitored. Detecting of the woman's heartbeat activates a display of a representation of the heartbeat and enables circuitry which displays a representation of the detected fetal heartbeat. Preferably two different types of sensors are used, for example an infra-red sensor for the woman's heartbeart and an audio sensor for the fetal heartbeat. The displays can depict hearts pulsating at rates corresponding with the respective heartbeats, or can present numerical displays of the heartbeat rates. In addition, a third sensor can detect movement of the fetus and can activate a display of a moving infant or a numerical display of the movement intensity or frequency. A combination of any of these displays can be presented. Signals representative of the detected heartbeats and movement can be recorded for later playback. A microphone and speaker permit the woman to provide audio stimulation to the fetus, and the fetal response to this stimulation can then be monitored.

39 Claims, 6 Drawing Sheets

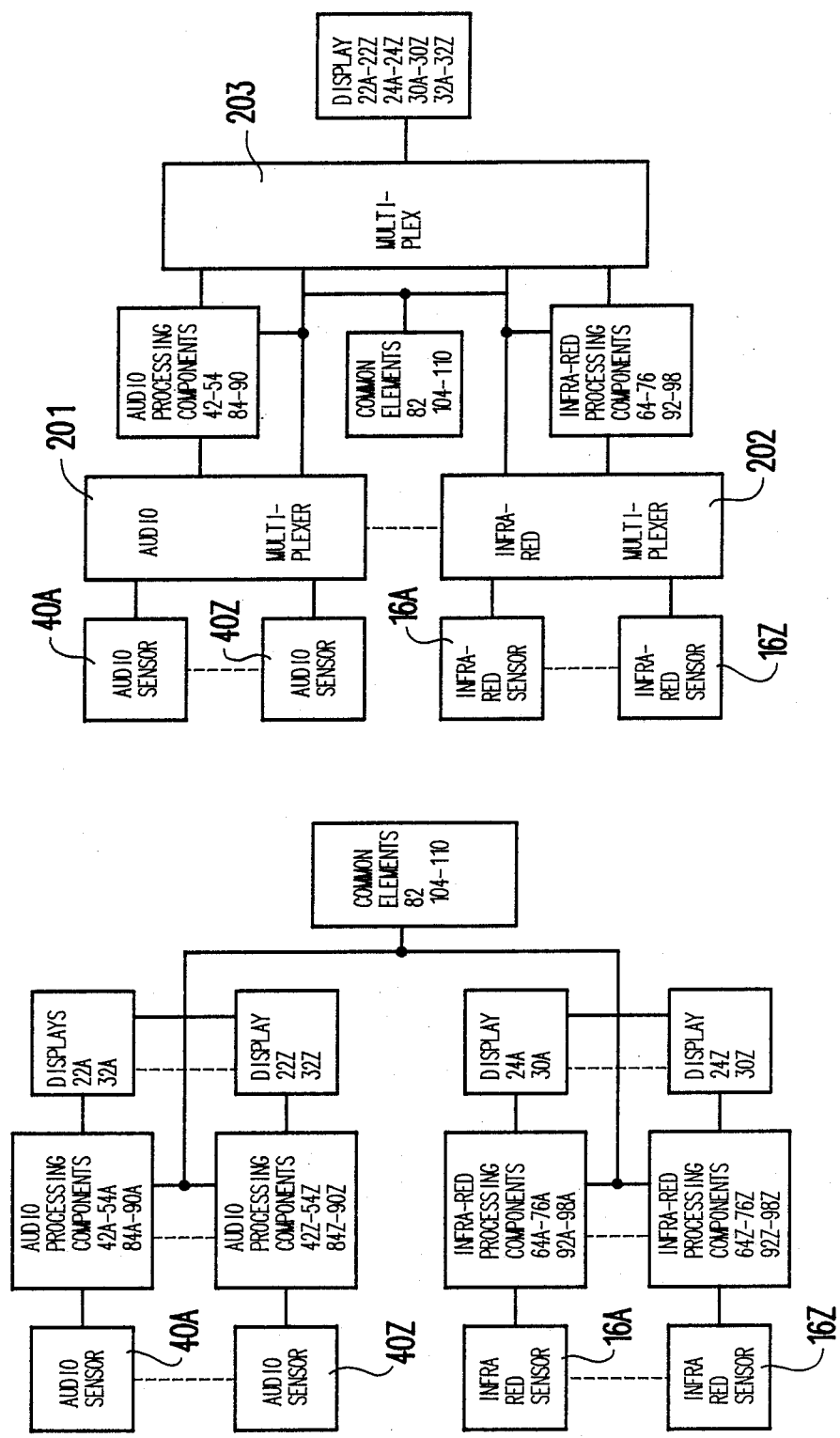

DEVICE FOR DETECTING, MONITORING, DISPLAYING AND RECORDING OF MATERIAL AND FETAL VITAL SIGNS AND PERMITTING COMMUNICATION BETWEEN A WOMAN AND HER FETUS

CROSS-REFERENCE TO RELATED APPLICATIONS

This application is a continuation-in-part of copending application Ser. No. 060,812 filed June 12, 1987, now abandoned, which, in turn, is a continuation-in-part of application Ser. No. 745,684, filed June 17, 1985, now U.S. Pat. No. 4,672,975 issued June 16, 1987.

BACKGROUND OF THE INVENTION

1. Field of the Invention

The present invention pertains to a device for monitoring fetal and maternal vital signs. More particularly, the present invention pertains to a device particularly suited for detecting, displaying, and recording a representation of the maternal and fetal heartbeats, fetal movement, and fetal response to external stimuli, dramatically improving communication between a mother and her fetus.

My U.S. Pat. No. 4,672,975 is directed to a stethoscope device which provides a visual indication of the heartbeat of an entity by displaying a representation of the heartbeat using two differently sized light members, superimposed one on the other. In a preferred version, each of the light members is in the shape of a heart, and detected heartbeats are utilized to produce electrical signals which control illumination of the heart-shaped light members to simulate a pulsating or beating heart.

In some circumstances it is necessary to display representations of two heartbeats. By way of example, it may be desired to display representations of the heartbeats of a pregnant woman and her fetus. In addition to the diagnostic benefit from such a display, an education benefit will also result. For example, such a display can be helpful in explaining the pregnancy to an older sibling. Such an activity can provide the older sibling with a feeling of acquaintance with the baby brother and sister it is soon to have and thus a willingness to welcome the younger sibling into the family.

2. Description of the Prior Art

Various different types of pulse rate sensing devices are known in the prior art. For example, U.S. Pat. No. 4,301,808, which issued to H. Taus on Nov. 24, 1981, discloses an infrared type sensor adapted to be attached to a body part of an exercising individual. The sensor is connected to drive digital, analog or flashing displays, which allow the individual to monitor their heart rate during exercise. U.S. Pat. No. 4,679,570, which issued to W. Lund et al on July 14, 1987, discloses a phonocardioscope which utilizes an acoustical sensor for producing an analog electrical signal in response to the sounds of heartbeats. The monitored heartbeats may be stored in RAM for display on an LCD, or for subsequent print out. German Offenlegungsschrift No. 2646414, published Apr. 28, 1977, discloses a stethoscope having a diaphragm disposed adjacent a sound chamber. Sounds of an individual's heartbeat are transmitted from the diaphragm through the sound chamber to conventional acoustic ear phones, and also to a pair of microphones situated in the chamber. Electrical signals from the microphones flash a lamp in response to detected heartbeats. A photodiode receives light impulses from the lamp and increments a self-resetting frequency counter, which provides a pulse rate display.

U.S. Pat. No. 3,945,373, which issued to D. Tweed et al. on Mar. 23, 1976, discloses an electro-optical transducer for converting displacements of an individual's body into an analog electrical signal.

None of these devices provide two separate sensors for simultaneously monitoring the pulse rates of a mother and a fetus. Additionally, the prior art devices do not disclose the use of interactive circuitry to prevent erroneous monitoring of the same pulse rate by both sensors.

SUMMARY OF THE INVENTION

The present invention is an improvement over the invention of my U.S. Pat. No. 4,672,975 in that the present invention provides at least two visual heartbeat displays of two different entities. The displays are interrelated in that one heartbeat, for example that of the expectant woman, must be detected first in order to enable display of the second heartbeat, such as that of the fetus.

The present invention is a device for detecting, displaying and recording representations of the heartbeat of a fetus in utero and with the heartbeat of the pregnant woman carrying the fetus. An audio sensor of the instrument is held against the woman's abdomen, in proper position to sense the fetal heartbeat, while the woman's heartbeat is detected via a finger placed through an elastic loop. A series of interactions between the two sensors enables the apparatus to ensure against falsely reading the woman's heartbeat, or other extraneous sounds, as that of the fetus. Firstly, the fetal heartbeat sensor does not function until a valid maternal heartbeat has been detected. Secondly, the fetal heartbeat display is not enabled unless a valid pulse rate sufficiently different from that of the woman is detected by the fetal heartbeat sensor. A manual override switch is provided for enabling monitoring of fetal heartbeat when simultaneous monitoring of maternal heartbeat is inconvenient or impossible, for example, in instances where the mother is dead and the fetus remains viable.

In addition, the apparatus senses and indicates fetal movement. The unit's displays indicate the occurrence, frequency, and intensity of the fetal movement. These fetal movement displays are not provided unless the mother's heartbeat and the fetal heartbeat displays have already been provided. Comparison of the movement with the changes in the fetal heartbeat ensures that the movement sensed is that of the fetus and not the mother. Thus, the interaction of the two heartbeat sensors and the fetal movement sensor prevents false indications of movement. If during the display of the fetal movement, the detected fetal heartbeat rate does not change, for example by increasing, then the fetal movement display is inhibited. A timing circuit may be provided for disabling the fetal movement display after a preselected time interval during which fetal heartbeat rate does not change. This would indicate that the fetal movement sensor is not sensing the true fetal movement, but instead is detecting vibrations induced by background noise. In such event, the mother can seek the true fetal movement elsewhere. An additional feature allows the introduction of an audible stimulus into the uterine cavity, enabling the simultaneous monitoring of fetal reaction as indicated by the heartbeat and motion.

With the device of the present invention, the difference in the rates of heartbeat of the two entities can be detected. For example, a pregnant woman can allow a child to listen and see a representation of the heartbeat of an unborn child's heartbeat rate compared to that of the pregnant woman. If desired, three heartbeats can be detected and displayed on three displays to permit the child to see and compare its own heartbeat with that of the woman and that of the unborn child.

The device of the present invention can use different types of pick-up sensors for the heartbeats, for example an audio pick-up device to be positioned on the abdomen of the pregnant woman to detect the sound of the fetal heartbeat and an infra-red pick-up device to be placed on the woman's finger to detect the woman's heartbeat by sensing the constriction and expansion of blood vessels in the finger. The device can provide various types of displays, for example numerical displays of heartbeat rates, a flashing light display having a heart shape, or a graphic display of a moving fetus.

The heartbeat of the pregnant woman must be detected before the fetal heartbeat can be displayed. As a result of this interaction, the two heartbeats cannot be confused.

The present invention also permits the application of external stimuli to the fetus and the monitoring of the fetal response. The Washington Times of Dec. 9, 1987, contains an article describing the Prenatal University at which a "Pregaphone" is used to transfer sounds directly to a fetus to stimulate the fetus to respond by kicking. However, the "Pregaphone" does not measure the effects of external stimuli on the fetus, and offers no way of telling whether the audio stimuli is too loud, or whether the fetus is asleep and being awakened. The advantages of the present invention over the "Pregaphone" device include that the present invention permits the monitoring and detection of the fetal response to external stimuli, thereby allowing an observer to discern between negative, potentially harmful stimuli, and positive, beneficial stimuli by measuring an increase or decrease of fetal heartbeat rate and movement.

By using the present invention, it is possible to learn about the fetal response to different kinds of stimuli, and possibly to discover the character of the fetus. Monitoring the fetal movement, and more specifically the quality and quantity of the fetus kicking, for example the strength and rate of kicking, gives some indication of the fetus's physical condition, for example the fetal weight, etc. By monitoring the fetus's heartbeat and movement over a long enough time period, it is also possible to learn about the fetus's sensitivity and emotions. There is little doubt that a normal fetus will react to outside information or stimuli differently than a fetus with mental or other abnormalities. The present invention permits audio stimulation of a fetus and also permits monitoring of the fetal response.

These and other objects, features, and advantages of the present invention are more apparent from the following description and claims, particularly when taken in connection with the accompanying drawings which show, for the purposes of illustration only, preferred embodiments of a heartbeat monitoring device in accordance with the present invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Each of the FIGS. 6 and 7 is a large scale functional block diagram illustrating the circuitry of an alternative embodiment of a stethoscope device in accordance with the present invention.

Figure 8:
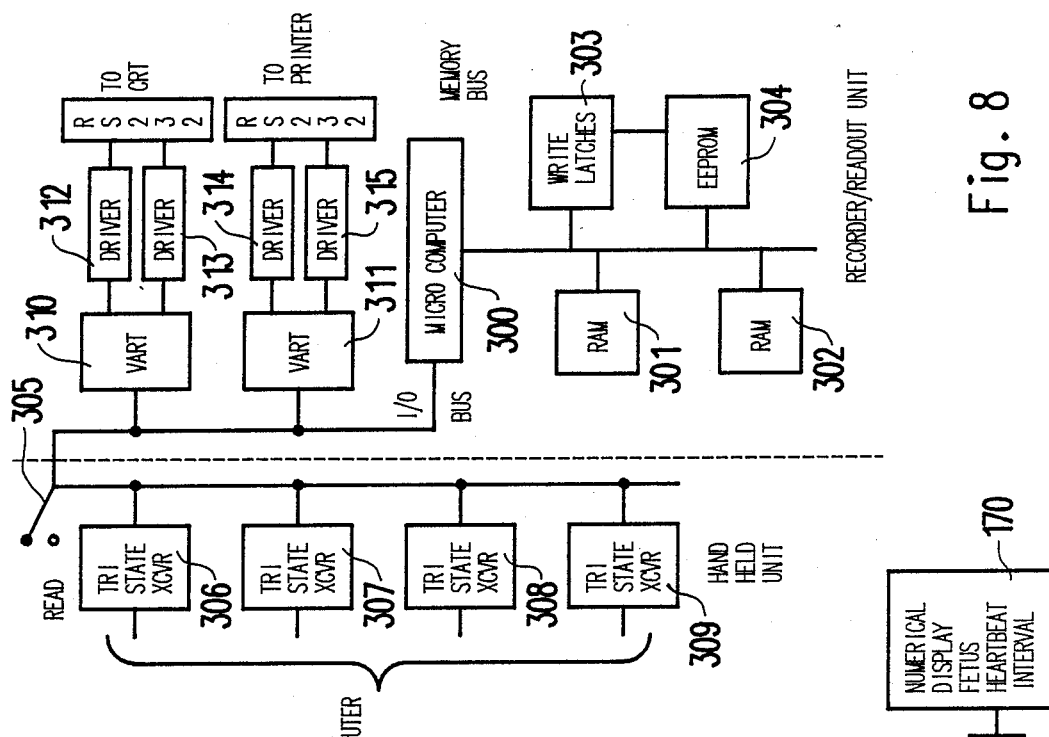
Figure 9:
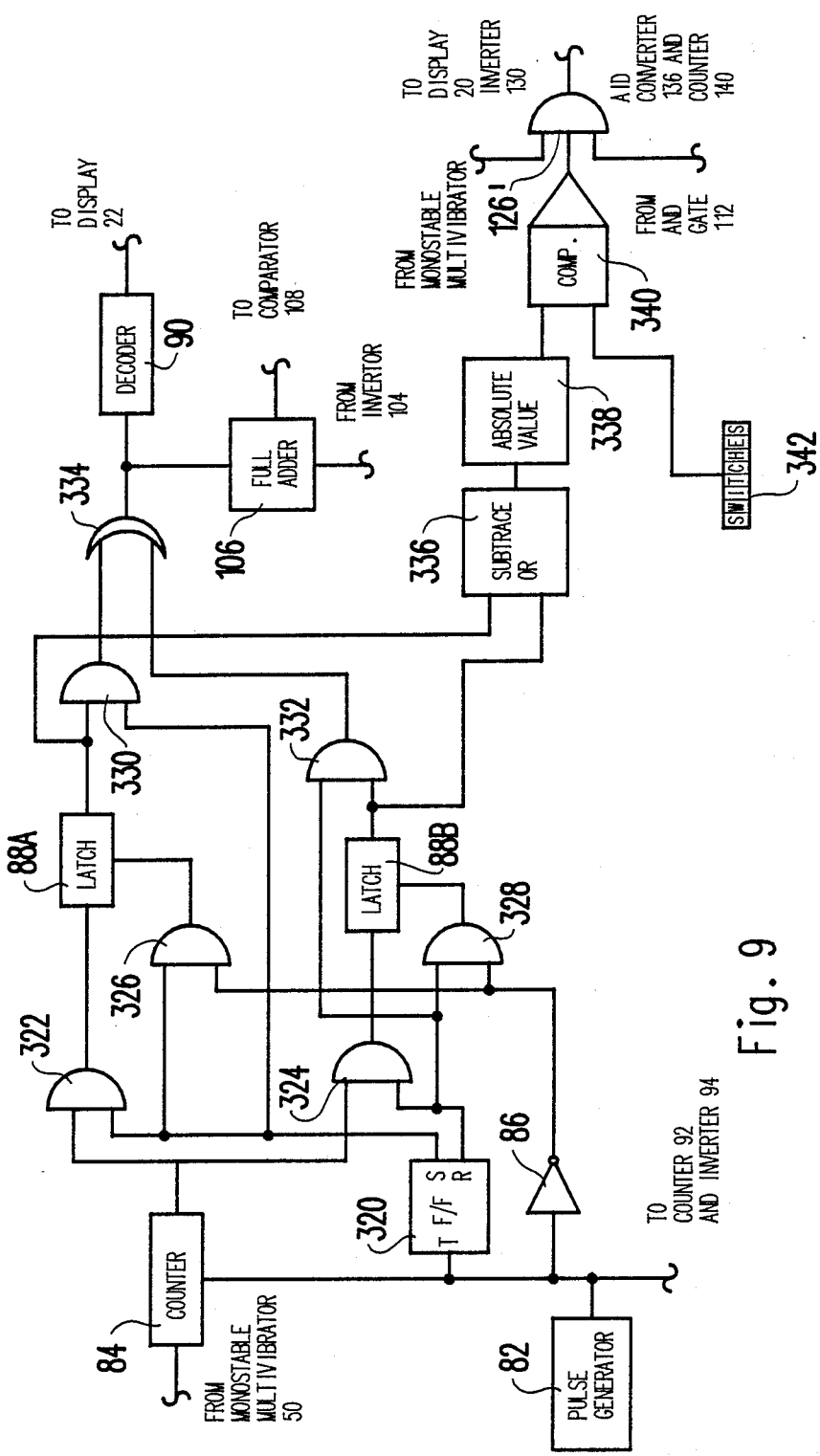

Each of the FIGS. 8 and 9 is a functional block diagram of additional circuitry usable in embodiments of the present invention.

DESCRIPTION OF THE PREFERRED EMBODIMENT

Figure 1:
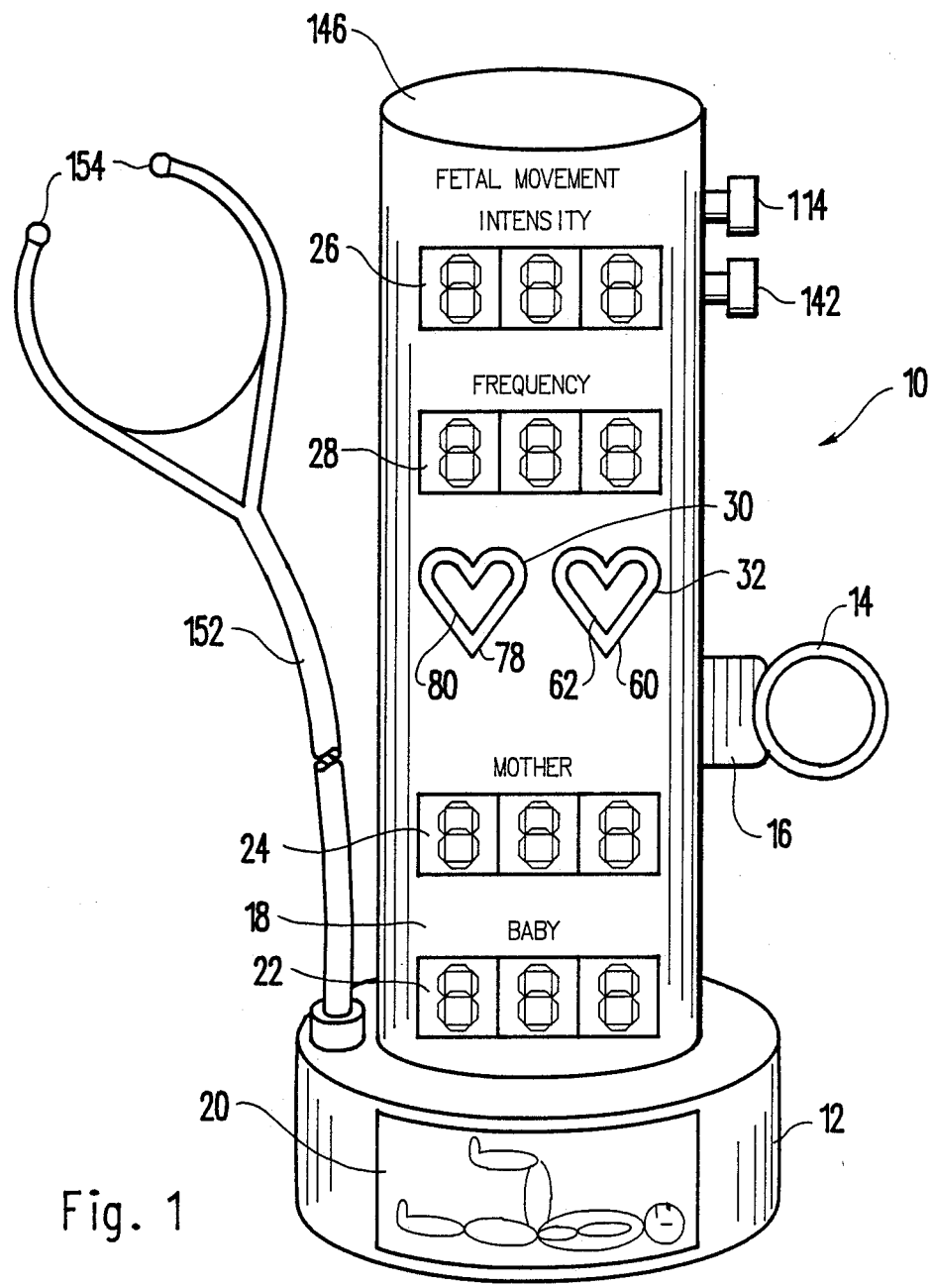
FIG. 1 is a front elevational view, partially in perspective, depicting a stethoscope device in accordance with one preferred embodiment of the present invention.

FIG. 1 illustrates a stethoscope device 10 in accordance with the present invention. Stethoscope 10 includes an audio detection chamber 12, a finger loop sensor 14 coupled to an infrared detector 16, and an electronics chamber 18. A number of displays are provided, including fetal movement display 20, fetal heartbeat rate display 22, the mother's heartbeat rate display 24, the fetal movement intensity display 26, fetal movement frequency display 28, the mother's movement indicator 30, and fetal heartbeat indicator 32.

Infra-red sensor 16 detects the maternal heartbeat through detection of the differences in infra-red reflectivity due to changes in the volume of blood in the capillaries of one of the mother's fingertips which is inserted in finger loop 14. This volume increases during systole, and decreases during the diastolic period. Thus, the occurrence of a systole may be detected and displayed.

Figure 2:
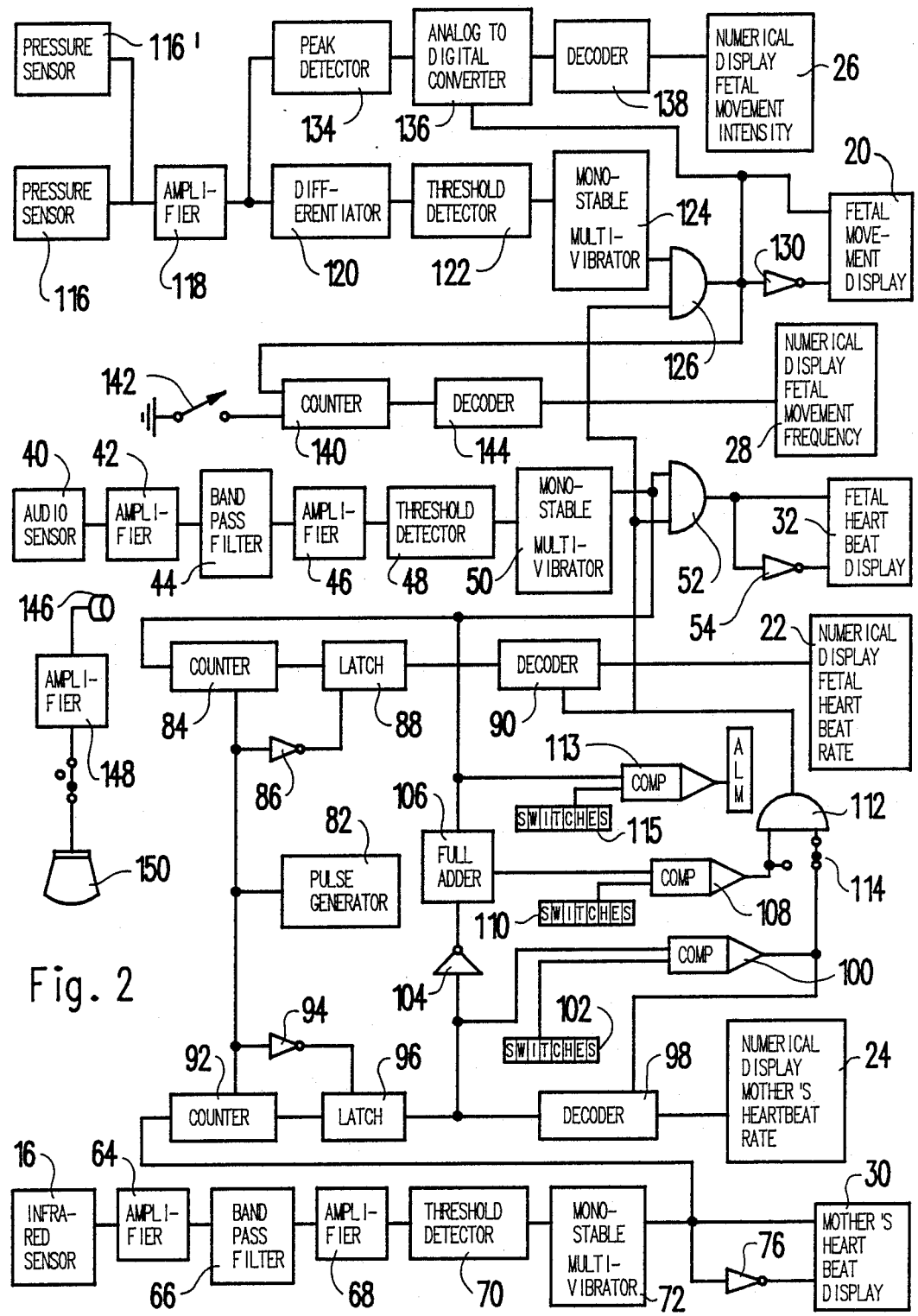
FIG. 2 is a functional block diagram of electronic circuitry suitable for incorporation into the stethoscope device of FIG. 1 in accordance with the present invention.

As seen in FIG. 2, amplifier 64 serves to increase the small differences in received infra-red amplitude as received from infra-red sensor 16. Filter 66 accentuates the small changes due to systole while removing spurious noise components. Amplifier 68 makes up for any losses in filter 66 and drives threshold detector 70. The threshold detector serves to discriminate between levels deemed to correspond to periods of systole and periods of diastole and produces a digital output indicating the current period (systolic or diastolic). This digital signal is applied to the input of the monostable multivibrator 72 which produces, for each input indicating systole, a fixed length output pulse sufficient in length to ensure the visibility of resulting display. The output of multivibrator 72 then drives LCD display 30 both directly and through invertor 76. As depicted in FIG. 1, display 30 can include a small, solid red heart-shaped light 78 so that alternate energization of lights 78 and 80 by the two inputs to display 30 depicts a pulsating heart. In addition, the signal developed by the monostable multivibrator 72 is simultaneously applied to the input of counter 92. The eight bit counter 92 is enabled by pulse generator of time base 82 for exactly 60 seconds. After the 60 seconds, counter 92 is disabled, and the accumulated count is transferred into the eight bit latch 96 which is enabled at that time via invertor 94. Counter 92 is then reenabled for the next count cycle, while the previous count is maintained stable in latch 96 for the duration of measurement period. The count in latch 96 is applied through decoder 98 to drive the numeric display 24. The output of latch 96 is also applied to one input of numeric comparator 100 which receives the output of switches 102 at its second input. Switches 102 flexibly set an acceptable heartbeat rate limit, and comparator 100 algebraically compares the limit set by switches with the current count in latch 96 and generates an alarm signal if the mother's heartbeat is at any unacceptably abnormal rate.

Sound transducer of audio sensor 40 is provided in the lower surface of audio detection chamber 12 to be audio coupled to the abdomen of the pregnant woman. This transducer detects an audible heartbeat and through amplifier 42, filter 44, amplifier 46 and threshold detector 48, triggers monostable multivibrator 50, the output of which is connected to the output of AND gate 112 such that gate 52 is enabled only when a valid mother's heartbeat and a valid fetal heartbeat have been detected. The output of AND gate 52 activates display 32 both directly, and through invertor 54 to provide a signal representative of the heartbeat on display 32. Just like the mother's heartbeat display 30, fetal heartbeat display 32 can include a small, solid red heart-shaped light 62 (FIG. 1) within a larger solid red heart-shaped light 60 so that alternate energization depicts a pulsating heart. Although displays 30 and 32 shown in the diagrams are suggested to be LCD displays, nothing in this description should be taken to indicate that similar displays using electroluminescent, LCD, or other technology cannot be substituted. Monostable multivibrator 50 detects the output of the threshold detector 48 and lengthens it into a fixed length digital pulse sufficiently long to effect a visible display. The signal developed by the monostable multivibrator 50 is simultaneously applied to the input of the eight bit counter 84. The 60 second pulses from pulse generator 82 enable counter 84 for the period of their duration; therefore the final count in counter 84 indicates fetal heartbeat directly. After 60 seconds, counter 84 is disabled, and the accumulated count is transferred into eight bit latch 88 which is enabled via invertor 86. Counter 84 is then reenabled for the next count cycle, while the previous count is maintained stable in latch 88 for the duration of the measurement period. The count in latch 88 is displayed on numeric display 22 whenever decoder 90 is enabled.

Decoder 90 provides the logic to convert the binary representation held in the latch 88 to the signals required to drive seven segment or equivalent numeric displays 22, as well as gating the display on only when a valid beat is detected by the proper interaction of the sensors, as described below.

The current maternal heart count in latch 96 is inverted or negated by eight invertors 104, and applied to one set of inputs of an eight bit full adder 106. The second set of inputs of adder 106 is fed directly from latch 88, which holds the current fetal heart count. The output of adder 106 is thus the difference between the maternal and fetal heartbeats. The normal fetal heartbeat is considerably faster than that of a normal adult, and this difference is fed to numeric comparator 108 which compares the magnitude of the difference to a preset threshold quantity contained in switch bank 110. If this magnitude is great enough, the fetal rate is considered valid. AND gate 112 receives the outputs from latch 96 and comparator 108. The output of AND gate 112 is connected to the enable input of decoder 90, turning on the fetal heartbeat display. If the difference between the maternal heartbeat count and the fetal heartbeat count is insufficient or nonexistent, or if a maternal heartbeat has not been previously detected, then the detected heartbeat is presumed to be that of the mother, and eecoder 90 remains gated off, disabling any fetal heartbeat display. Thus, this interaction between the sensor channels allows the presentation of only validated fetal heartbeats. Maternal override switch 114, positioned on electronics chamber 18, permits the maternal heartbeat validity check to be eliminated in those cases where it is impossible or undesirable to obtain a valid maternal heartbeat, for example in cases where the mother is dead, or desires to have her hands free from the infrared detecting loop 14 while providing audi stimuli to the fetus through microphone 146.

The fetal heartbeat count in latch 88 is also applied to one input of comparator 113, the second input of which receives a signal determined by the settings of switches 115. Comparator 113 thus provides an alarm signal in response to an abnormal fetal heartbeat rate.

Fetal movement is detected by pressure sensor 116 which is a voltage divider composed of a fixed resistor and a broad area force sensing resistor screen printed on a polyester substrate and glued to the lower surface of audio detection chamber 12 of the stethoscope unit 10. A second pressure sensor 116' may be provided either instead of, or in addition to the first sensor 116. The sensor 116' is removably connected by an extension cable 117 (FIG. 3) having a conventional electrical connection jack (not shown) to the body of the stethoscope 10. This enables physical separation and independent optimal placement of the fetal heart rate sensor and the fetal movement sensor on the mother's abdomen. Suitable switching circuitry may be provided for selecting operation with either sensor 116 or 116'. The resistance of the force sensing resistor is proportional to the force normal to the base of the stethoscope. This force is composed of the steady force of the instrument's application to the abdomen, pulse forces acting from inside the abdomen, primarily resulting from fetal movement inside the uterus. The output of the voltage divider is therefore a voltage proportional to these forces. This voltage is buffered by amplifier 118, and differentiated by differentiator 120, resulting in a voltage indicating the rate of change of these forces. This voltage is applied to threshold detector 122 which differentiates between a rate of change high enough to indicate the sharp, quick increase of pressure characteristic of a fetal movement against the sensor, and the slower, more gradual changes in pressure due to changes in hand pressure, and other changes within the abdomen. The digital output of threshold detector 122 is applied to a monostable multivibrator 124 which provides for each input indicating a fetal movement of a fixed length output pulse of sufficient duration to ensure the visibility of the resulting display. The output of multivibrator 124 is then applied to one input of AND gate 126 which receives the output from AND gate 112 at its other output. The output of AND gate 126 is applied directly to fetal movement display 20 and also through invertor 130 to display 20. Display 20 is then indicated in FIG. 1 as depicting the figure of an infant, with a knee that appears to move when a fetal movement is detected. Other forms of display indication may also be used. AND gate 126 gates the fetal movement signal with the "Fetal Heartbeat Valid" signal from AND gate 112, thus ensuring that the probe is in the vicinity of the fetus when a movement is indicated. The output of AND gate 126 is also applied to counter 140 which counts the number of detected fetal movements. The counter thus indicates the frequency of fetal activity detected, which may then be easily correlated with the changes in the displayed fetal heartbeat. The counter state is decoded by decoder 144 and displayed on numeric display 28. Counter 140 can be manually reset by switch 142 positioned on electronics chamber 18 (FIG. 1).

The output of amplifier 118 is also applied to peak detector 134. This sample and hold device records the peak pressure reached in any short time interval due to fetal movement. The magnitude of the peak pressure achieved during the movement is converted to a digital quantity by analog to digital converter 136 which is gated by the output of AND gate 112. The resulting digital value is then converted to a seven segment or other numeric display 26, resulting in a numeric display of the relative strength of fetal activity, validated by interaction with the other sensors.

Microphone 146 is provided so that an arbitrary audible stimulus may be introduced into the uterine cavity at will. Microphone 146 can be positioned in the top surface of electronics chamber 18 (FIG. 1) or can be a separate, hand-held unit connected to the electronics chamber by appropriate wiring. This stimulus is amplified by amplifier 148 and presented to the uterine cavity via speaker 150, which is within the lower surface of audio detecting chamber 12 and is in correct position. Audio baffles and differences in operating frequency prevent these two transducers from interfering with one another. This permits audible stimulus to be introduced in the uterine cavity and the fetal response to that stimulus to be monitored with the same instrument. The amplifier may be fitted within the capability of accommodating numerous audio sources other than a microphone, including but not limited to various forms of electronic music reproduction and/or generation devices, and various forms of arbitrary electronic waveform generators. Thus, nothing in this description should be construed as limiting the range of audio sources which can be utilized as stimuli. Before utilizing microphone 146, amplifier 140, and speaker 150 to stimulate the fetus, the fetal condition should be monitored with stethoscope 10 to assure it is in proper condition for the stimulation.

Nothing in this description is intended to indicate that the various displays need be separate units, but, as shown in FIG. 1, these may be concentric, possibly heart-shaed areas on a specially prepared display device. In FIG. 1, finger loop 14 is used to securely maintain the position of the finger with respect to the infrared sensor device. Loop 14 is placed such that the device can be conveniently held with one hand, one finger of which is placed within the loop for the purpose of measuring the maternal heartbeat. The display is oriented such that it can be conveniently observed by the mother during such use.

As seen in FIG. 1, a stethoscope tube 152 can be used to couple chamber 12 to ear tips 154 to permit the stethoscope device 10 to be utilized as a standard stethoscope. In addition, if desired, an audio tape recorder can be incorporated to record the heartbeats and to play them back through speaker 150 for later comparison with more recent heartbeats. This could be done in a manner which permits the playback to activate indicators 30 and 32, if desired. The taped heartbeats played back on the speaker could also be utilized by a doctor as a diagnostic tool. By way of example, the heartbeats could be played over the telephone to enable a doctor to listen to the heartbeat rate.

Figure 3:
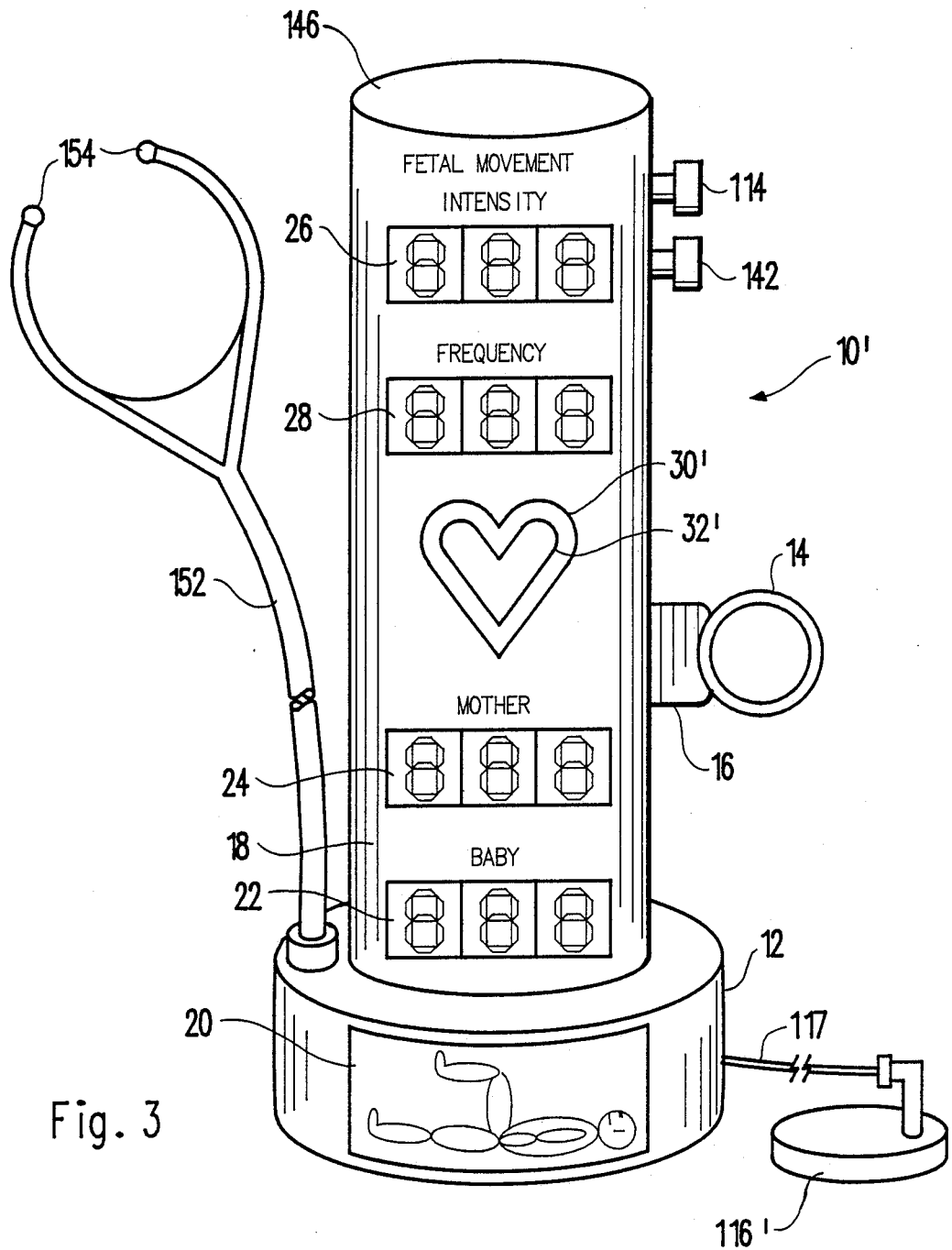
FIG. 3 is a front elevational view, partially in perspective, of a second preferred embodiment of the present invention.
Figure 4:
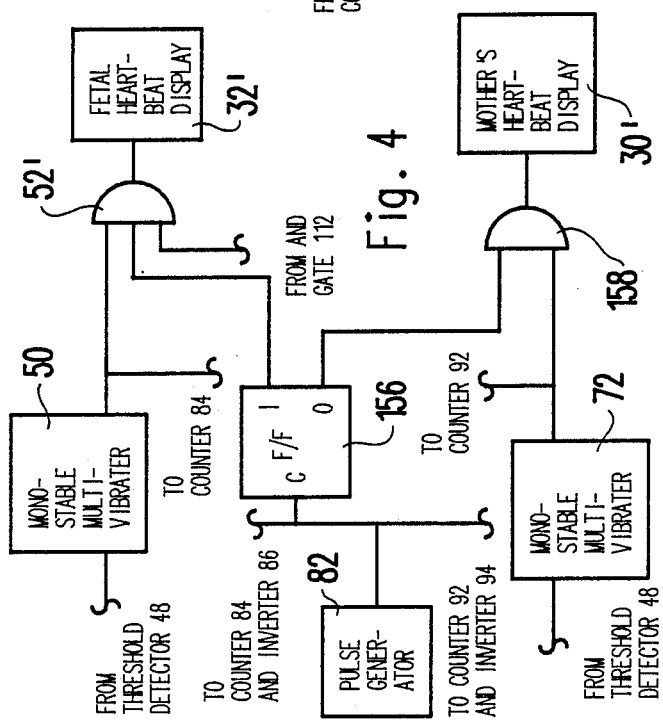
FIG. 4 is a fragmentary functional block diagram of electronic circuitry suitable for incorporation into the embodiment of FIG. 3.

FIG. 3 shows an alternative embodiment of a stethoscope device 10' in accordance with the present invention. Rather than providing the mother's heartbeat display 30 with smaller heart 80 within larger heart 78 and the fetal heartbeat display 32 with smaller heart 62 within larger heart 60, as in FIG. 1, stethoscope device 10' has a fetal heartbeat display 32' in the from of a red heart-shaped light member. FIG. 4 depicts circuitry suitable for implementing displays 30' and 32'. Those portions of the circuitry of FIG. 2 that are not changed are not repeated in FIG. 4; instead only the modifications to the circuitry of FIG. 2 are depicted in FIG. 4.

The output from pulse generator 82 goes to counters 84 and 92 and to invertors 86 and 94, just as in FIG. 2. In addition, the pulse generator 82 output is applied to the clock input of bistable multivibrator or flip-flop 156. The output from monostable multivibrator 50 is applied to counter 84 and to input of AND gate 52' which also receives the output from AND gate 112, just as does AND gate 52 of FIG. 2. In addition, AND gate 52' receives the 1 output from flip-flop 156. The output of AND gate 52' activates fetal heartbeat display 32'.

The output of monostable multivibrator 72 goes to counter 92, just as in FIG. 2, and also to one input of AND gate 158. The 0 output of flip-flop 156 is connected to the second input of AND gate 158. The output of AND gate 158 activates the mother's heartbeat display 30'.

Each 60 second pulse from pulse generator 82 is used by counters 84 and 92 and latches 88 and 96 and associated circuitry to provide the mother's and fetal heartbeat rate indications on displays 22 and 24, just as in the circuitry of FIG. 2. In addition, with each 60 second pulse from pulse generator 82, flip-flop 156 is clocked, and so the mother's heartbeat display 30' and the fetal heartbeat display 32' are enabled during alternating 60 second intervals to providing pulsating representations of the respective heartbeats.

Various types of display devices can be utilized for displays 20, 22, 24, 26 and 28, including LEDs and LCDs. Decoders 90, 98, 138 and 144 decode the digital signals from their respective inputs to the appropriate activation signals for their associated displays 22, 24, 26 and 28 which, by way of example, might be seven segment displays. Other detailed circuitry required for specific types of display devices must, of course, be provided. Various optimization techniques might result in alterations to the detailed circuitry, but the presently preferred logic is shown in FIGS. 2 and 4.

If desired, the membrane covering the lower end of chamber 12, which contacts the mother's abdomen, can be selected to filter the mother's heartbeat while passing the more rapid fetal heartbeat, aiding in the selectivity of the device.

Figure 5:
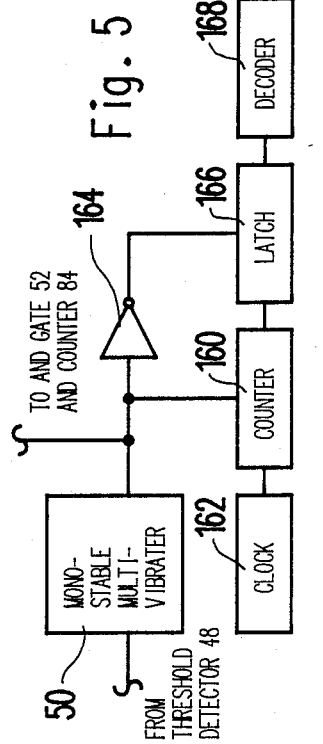
FIG. 5 is a functional block diagram of circuitry to provide an additional indication during heartbeat monitoring.

The time interval between heartbeats may also be of interest. FIG. 5 depicts circuitry for providing such a display. The output of monostable multivibrator 50, which as seen in FIG. 2 is triggered each time a fetal heartbeat is detected, is applied to the reset input of counter 160 which receives clock pulses from clock 162 at its count input. The clock pulses might be at 100 ms intervals, for example. The output of monostable multivibrator 50 also passes through invertor 164 to the enable input of latch 166 which receives the output of counter 160 at its signal input. The output of the latch 166 is connected to decoder 168, the output of which is applied to fetal heartbeat interval display 170. Thus, the number of clock pulses occurring between consecutive fetal heartbeats is displayed as a time reading in seconds and tenths of a second on display 170. A similar circuit can be provided for the mother's heartbeat, if desired.

In some applications, for example, monitoring the heartbeat of twin fetuses, it may advantageous to have two or more of any one or all of the sensors. A scheme for implementing such an instrument is shown in simplified form in FIG. 6. This diagram indicates the construction of an instrument having two or more sound transducers 116a . . . 116z, each of which has its own replicated signal processing electronics and display. This technique provides a continuous display of readouts of all channels simultaneously. For clarity, most of the detail of the prior figures has been omitted, as has the fetal pressure sensing mechanism. This should not be construed as indicating that all of these features cannot be combined in a single instrument, nor that the use of multiple sensors cannot be extended to the pressure sensor. Each transducer and its associated electronics may be thought of as a separate "channel", and in FIG. 6 each channel is distinguished by a letter suffix. Thus, infra-red transducer 16A is associated with infra-red channel A, and drives processing elements 64A–76A and 92A–98A which in turn drive displays 24A and 30A. A second infra-red channel includes sensor 16B, electronics 64B–76B and 92B–98B and displays 24B and 30B, and so on through channel Z or more. An identical nomenclature is used for the sound channels, and a similar technique could be used for the fetal pressure sensor as well. Each of the elements of each channel has the same functions as the like numbered components of the preceding figures. Similarly, audio sensors 40A . . . 40Z are coupled through electronics 42A–54A, 84A–90A . . . 42Z–54Z, 84A–90Z to display 22A, 32A . . . 22Z, 32Z, and pressure sensors 116A . . . 116Z are coupled through electronics 118A–144A . . . 118Z–144Z to displays 20A, 28A . . . 20Z, 28Z. Elements 82A, 104A–110A . . . 82Z, 104Z–110Z are likewise provided, although a single pulse generator 82 can be used, if desired. It is assumed here that the sources of the various heartbeats are distinct, and that the output of each sensor represents a single heartbeat, so that it is not necessary to determine which beats are associated with which rhythm. This will always be the case if, for example, two infra-red sensors are used to sense the heartbeats of different members of a family, presenting a display of the entire family's heart condition, and will generally be true for the case of multiple sound transducers used for multiple fetuses, since, in general, unique positions for the individual transducers can be found which yield optimal sound pickup for one fetus, while reducing the sound of the second to insignificant noise which may be easily filtered.

Several configurations of the enabling circuitry 104 through 110 are possible in these variations, depending upon intended use. If additional infra-red sensors are used, but only one is intended to measure the maternal heartbeat, that one may be connected to the maternal input of the comparator circuitry, and the enable signal used to gate all audio sensor channels. This would be the case in an instrument designed for simultaneous monitoring of multiple fetuses, for example. It may be desirable to logically or arithmetically combine the outputs of multiple maternal sensors, using, for example, the lowest rate as the maternal input to the comparator, when for example, the multiple sensors are positioned at different points on the individual, for reliability, or the detection or monitoring of unusual or pathologic conditions in which the perceived heart rate varies at different locations on the body. All such extensions are included in this application, notwithstanding that all possible variations have not been explicitly mentioned, or diagrammed.

FIG. 7 shows a variation in which the transducer outputs are viewed sequentially rather than simultaneously. This provides reductions in cost, weight, and power consumption. FIG. 7, like FIG. 6, omits much detail which has been presented earlier. In FIG. 7 transducers 40A through 40Z are multiplexed to a single set of processing elements 42–54, 84–90, and similarly, transducers 16A through 16Z are multiplexed to a single set of processing elements 64–76, 92–98. This is accomplished by multiplexors 201 and 202 respectively, which sequentially connect one transducer at a time to the related electronics, under control of the common elements 82 and 104–110. Each set of processing elements could then drive its own set of displays 22A–22Z, 24A–22Z, 30A–30Z, 32A–32Z, or a single set of displays 22, 24, 30, 32 may be used with an additional multiplexor 203 used to connect one set of processing elements to it at a time. Again, use of the enabling and comparator circuitry 104 through 110 will be dependent upon the application. This scheme lends itself well to the case where it is desirable to pair maternal and fetal indicators, with each fetal indicator controlled by a separate maternal indicator enabled coincidentally.

The construction of such a multi-channel unit can follow a somewhat different design than presented earlier. Multi-channel units are most sensibly built with all electronics in a desk top sized standard cabinet or box and a set of connectors for a variable number of remote transducers. Connectors are therefore shown for all transducers on the diagrams though they are not required for operation.

An optional recording unit is shown in block diagram form in FIG. 8. The recording unit will read all digital counters within the stethoscope unit on command, and record them, together with the date and time, in a nonvolatile solid state memory, from which they may later be read out on an external computer or CRT terminal. This is of importance in the case where it s desirable to monitor the activity and vital signs of the fetus between medical visits. The obstetrician may direct the mother to measure and record the various vital signs at fixed intervals or upon the occurrence of certain specified conditions. These will be stored within the memory unit until the next regular visit, when the doctor may read this information out onto a CRT or personal computer kept in his office. Optionally, the readings may be printed on an auxiliary printer which may be connected to the recording unit as well.

The unit with recording option is operated identically to the unit previously described. The desired readings are recorded in the separate recording unit, which is connected to the hand held unit by a flexible multi-wire cable. This recording can be done automatically or in response to actuation of a pushbutton. The doctor can rely upon these readings to be that of the fetus rather than that of the mother, even though obtained through the inexperienced measurements of the mother or her family, because of the safeguards provided by the interaction of the multiple sensors, as described previously.

As illustrated in FIG. 8, the option consists of separate recorder/readout unit, interface circuitry in the hand held unit, and a flexible cable between the units. The recorder/readout unit houses a single chip microcomputer 300 that controls the recording and storage operations, a 2 kilobyte RAM memory 301, which provides a program scratchpad, and an 8 kilobyte RAM memory 302 used to store the fixed program that directs the microcomputer to perform its various operations. The single chip computer 300 is chosen to be of a type which implements two buses, as illustrated, one for input/output (I/O), and the other for internal memory operations, as opposed to an implementation of the common memory-mapped I/O scheme. This provides a simpler, slower I/O bus, that can be extended to the hand held unit with a relatively small number of wires. In addition, the microcomputer contains a battery operated real-time clock, which once set to the correct date and time, makes that continuously updated information available to the stored program upon command.

The heart of the device, however, is the 8 kilobyte electrically erasable programmable read only memory, or EEPROM 304. This device allows the reliable long term storage of readings taken over the course of time, and provides reliable storage in the face of power losses. The EEPROM writer latches 303 are used to hold the data during several milliseconds that it may take to write the data into the EEPROM device, since the microcomputer 300 normally holds write data available for only the one or two microseconds that it takes to write data into the volatile RAM memory. Control of the recorder/readout unit in the physician's office is provided through the connection of an external CRT terminal and keyboard, via the RS-232 serial port implemented by UART (Universal Asynchronous Receiver Transmitter) 310, line driver 312, and line receiver 313.

Using commands interpreted by the stored program in ROM 302, the user physician can read the raw data stored by the user mother in EEPROM 203, direct that it be printed via UART 311, driver 314, and receiver 315 to an external serial printer, direct that the raw data be scanned for preprogrammed anomalous conditions, or be statistically summarized, with the summaries and/or anomalous conditions only, —displayed and/or printed out.

The capture of the data itself is provided by tri-state bus transceivers 306–309. These are located in the hand held unit, and attached directly to the three counters (FIG. 2, items 84, 92 and 140) and the output of the A/D converter (FIG. 2, item 136), and gate the readings of the counters and converter onto the microcomputer as directed by the stored program. AT appropriate intervals, microcomputer 300 generates an interrupt signal on the I/O bus, which causes the microcomputer to execute the program portion which reads the counters and stores the readings in the EEPROM together with the date and time. This program segment, however, performs preprogrammed logical checks on the readings before recording them, so that the previously described interactions between the sensor readings are maintained for the recorded data. In addition, more stringent checks can be performed by the program, including the specification of more flexible interrelationship criteria, and range checking for all variables.

FIG. 9 is a functional block diagram depicting circuitry for inhibiting the fetal movement displays when the detected fetal heartbeat is not increasing as would be expected as a result of such movement. Again, those portions of the circuitry of FIG. 2 that are not changed are not repeated in FIG. 9 but only the modifications of FIG. 2 are depicted in FIG. 9.

The output of pulse generator 82 is applied to the toggle input of bistable multivibrator or flip-flop 320. Counter 84 applies its output to one input of AND gate 322, and to one input of AND gate 324. The set output of flip-flop 320 is connected to the second input of AND gate 322, while the reset output of the flip-flop is connected to the second input of AND gate 324. The output of AND gate 322 is connected to the input of latch 88a, and the output of AND gate 324 is connected to the input of latch 88b. The output of pulse generator 82 is also passed through invertor 86 to one input of each of AND gate 326 and AND gate 328. The second input of AND gate 326 is connected to the set output of flip-flop 320, while the second input of AND gate 328 is connected to the reset output of the flip-flop. The output of AND gate 326 is connected to the enable input of latch 88a, and the output of AND gate 328 is connected to the enable input of latch 88b. The output of latch 88a is connected to one input of AND gate 330, the second input of which is connected to the set output of flip-flop 320. The output of latch 88b is connected to one input of AND gate 332, the second input of which is connected to the reset output of flip-flop 320. The outputs of AND gate 330 and 332 are connected through OR gate 334 to decoder 90 and to full adder 106.

With each pulse from pulse generator 82, flip-flop 320 toggles between its set condition and its reset condition, and so the latch 88z and latch 88b are alternately enabled to store the count in counter 84 and to apply that count to decoder 90 and to full adder 106. Decoder 90 and adder 106 and the subsequent circuitry then function as in FIG. 2.

The outputs of latches 88a and 88b are applied to the two inputs of subtractor 336, the output of which is passed through absolute value circuit 338 to give the absolute value of the difference between the count stored in latch 88a and the count stored in latch 88b. This absolute value thus indicates the difference in the fetal pulse rate from one output pulse of generator 82 to the next.

The absolute value difference signal from circuit 338 is applied to one input of numeric comparator 340, the second input of which receives the output of switches 342. The output of comparator 340 is connected as a third input to AND gate 120 of FIG. 2. Thus, unless the fetal heartbeat rate is increasing at a rate determined by the setting of switches 342, gate 126' is blocked, and fetal movement display 20, fetal movement intensity display 26 and fetal movement frequency display 28 are not activated. In such case fetal movement display 20 would display a baby lying inactive. If the mother feels fetal movement and is getting a fetal heartbeat rate display but no fetal movement display, she knows that movement sensor 116 is sensing something other than the fetal movement, and so she can reposition device 10 to enable sensor 116 to pick up the fetal movement. A timing circuit may be provided for disabling the fetal movement display after a preselected time interval during which fetal heartbeat rate does not change. This would indicate that the fetal movement sensor is not sensing the true fetal movement, but instead is detecting vibrations induced by background noise.

Although the present invention has been described with reference to a preferred embodiment, modifications and rearrangements could be made, and still the result would come within the scope of the invention.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An obstetrical device for monitoring and displaying a representation of the heartbeats of a pregnant woman and her fetus, said device comprising:
   a first sensor circuit for detecting the heartbeat of the pregnant woman and generating a first electrical signal representative of that heartbeat;
   first display means connected to said first sensor circuit and responsive to the first electrical signal for providing a first visual signal representative of the pregnant woman's heartbeat;
   a second sensor circuit for detecting the heartbeat of the fetus and generating a second electrical signal representative of that heartbeat;
   an enabling circuit having an input connected to said first sensor circuit and having an output, said enabling circuit responsive to the first electrical signal for generating an enabling signal on said enabling circuit output; and
   second display means connected to said enabling circuit output and to said second sensor circuit and responsive to the second electrical signal during the presence of the enabling signal for providing a second visual signal representative of the fetal heartbeat.

2. A device as claimed in claim 1, wherein said first sensor circuit includes an infra-red sensor.

3. A device as claimed in claim 2, wherein said second sensor circuit includes an audio sensor.

4. A device as claimed in claim 1, wherein said second sensor circuit includes an audio sensor.

5. A device as claimed in claim 1, wherein said first display means includes a first display device depicting a first heart pulsating at a rate corresponding with the rate of the woman's heartbeat and said second display means includes a second display device depicting a second heart pulsating at a rate corresponding with the rate of the fetal heartbeat.

6. A device as claimed in claim 5 wherein:
   said first display device comprises a first heart-shaped display member for generating a visual display of a first heart, a second heart-shaped display member for generating a visual display of a second heart within the display of the first heart, and means responsive to the first electrical signal for alternately energizing said first heart-shaped display member and said second heart-shaped display member at a rate substantially equal to the rate of the woman's heartbeat to represent a heart contracting at the rate at which the woman's heart is beating; and
   said second display device comprises a third heart-shaped display member for generating a visual display of a third heart, a fourth heart-shaped display member for generating a visual display of a fourth heart within the display of the third heart, and means responsive to the second electrical signal for alternately energizing said third heart-shaped display member and said fourth heart-shaped display member at a rate substantially equal to the rate of the fetal heartbeat to represent a heart contracting at the rate at which the fetal heart is beating.

7. A device as claimed in claim 6 wherein each heart-shaped display member, upon energization, depicts a substantially solid, colored representation of a heart.

8. A device as claimed in claim 5 wherein:
   said first display device comprises a first heart-shaped display member for generating a visual display of a first heart;
   said first display means further includes means responsive to the first electrical signal for alternately energizing and deenergizing said first heart-shaped display member to represent the woman's heart beating at a rate substantially equal to the rate of woman's heartbeat;
   said second display device comprises a second heart-shaped display member for generating a visual display of a second heart within the display of the first heart; and
   said second display means further includes means responsive to the second electrical signal for alternately energizing and deenergizing said second heart-shaped display member to represent the fetal heart beating at a rate substantially equal to the rate of the fetal heartbeat.

9. A device as claimed in claim 8 wherein each heart-shaped display member, upon energization, depicts a substantially solid, colored representation of a heart.

10. A device as claimed in claim 1 wherein said first display means includes a first numerical display for numerically displaying the woman's heartbeat rate.

11. A device as claimed in claim 10 wherein said second display means includes a second numerical display for numerically displaying the fetal heartbeat rate.

12. A device as claimed in claim 1 wherein one of said first and second display means includes a numerical display for displaying the time interval between consecutive one of the associated detected heartbeats.

13. A device as claimed in claim 1 wherein said first sensor circuit incudes means for generating an alarm signal when the detected woman's heartbeat is at an abnormal rate.

14. A device as claimed in claim 1 wherein said enabling circuit includes means for inhibiting generation of the enabling signal when the difference between the rate of the detected fetal heartbeat and the rate of the detected woman's heartbeat is below a preset amount.

15. A device as claimed in claim 1 wherein said second sensor circuit includes means for generating an alarm signal when the detected fetal heartbeat is at an abnormal rate.

16. A device as claimed in claim 1 further comprising:
a third sensor circuit for detecting movement of the fetus and generating a third electrical signal representative of the movement; and
third display means connected to said enabling circuit output and to said third sensor circuit and responsive to the third electrical signal during the presence of the enabling signal for providing a third visual signal representative of the fetal movement.

17. A device as claimed in claim 16 wherein said third sensor circuit includes a pressure sensor.

18. A device as claimed in claim 16 wherein said third display means includes a visual display device depicting a representation of the fetus.

19. A device as claimed in claim 16 wherein said third display means includes a numerical display for numerically displaying the intensity of the fetal movement.

20. A device as claimed in claim 16 wherein said third display means includes a numerical display for numerically displaying the frequency of the fetal movement.

21. A device as claimed in claim 16 wherein said enabling circuit includes means for inhibiting generation of the enabling signal if the detected fetal heartbeat is not changing during fetal movement measurement.

22. A device as claimed in claim 16 wherein said third sensor circuit includes a plurality of sensing elements for sensing a like plurality of fetal movements and a multiplexor for generating the third electrical signal in sequential response to each of the plurality of fetal movements.

23. A device as claimed in claim 16 further comprising means for recording signals indicative of the fetal heartbeat and movement, and means for playing back the recorded fetal heartbeat and movement signals.

24. A device as claimed in claim 23 further comprising means for recording signals indicative of the woman's heartbeat and means for playing back the recorded woman's heartbeat signals.

25. A device as claimed in claim 16 further comprising means for determining the rate of change of the fetal heartbeat rate and means for inhibiting said third display means when the rate of the change of the fetal heartbeat rate is less than a predetermined amount.

26. A device as claimed in claim 1 further comprising;
a microphone;
a speaker coupled to said microphone for providing audio signals corresponding with sounds detected by said microphone;
means positioning said speaker adjacent said second sensor circuit to permit providing of audio stimulation to the fetus and detection and recording of the effects of such audio stimulation on the detected fetal heartbeat.

27. A device as claimed in claim 16 further comprising;
a microphone;
a speaker coupled to said microphone for providing audio signals corresponding with sounds detected by said microphone;
means positioning said speaker adjacent said second sensor circuit to permit providing of audio stimulation to the fetus and detection and recording of the effects of such audio stimulation on the detected fetal heartbeat.

28. A device as claimed in claim 1, wherein said first sensor circuit includes a plurality of sensing elements for sensing a like plurality of heartbeats and a multiplexor for generating the first electrical signal in sequential response to each of the plurality of heartbeats.

29. A device as claimed in claim 28 wherein said second sensor circuit includes a plurality of sensing elements for sensing a like plurality of fetal heartbeats and a multiplexor for generating the second electrical signal in sequential response to each of the plurality of fetal heartbeats.

30. A device as claimed in claim 1 wherein said second sensor circuit includes a plurality of sensing elements for sensing a like plurality of fetal heartbeats and a multiplexor for generating the second electrical signal in sequential response to each of the plurality of fetal heartbeats.

31. A device as claimed in claim 1 further comprising means for recording signals indicative of the fetal heartbeat and means for playing back the recorded fetal heartbeat signals.

32. A device as claimed in claim 31 further comprising means for recording signals indicative of the woman's heartbeat and means for playing back the recorded woman's heartbeat signals.

33. A device as claimed in claim 1 further comprising means for recording signals indicative of the woman's heartbeat and means for playing back the recorded woman's heartbeat signals.

34. An obstetrical device for monitoring and displaying a representation of the heartbeats of a pregnant woman and her fetus, said device comprising:
a first sensor circuit including an infra-red sensor for detecting the heartbeat of the pregnant woman and generating a first electrical signal representative of that heartbeat;
a first display device including a first substantially solid red, heart-shaped display member for generating a visual display of a first heart and a second substantially solid red, heart-shaped display of a second heart within the first heart, said first display device connected to said first sensor and responsive to the first electrical signal for alternately energizing said first heart-shaped display member and said second heart-shaped display member at a rate substantially equal to the rate of the woman's heartbeat to represent a heart contracting at the rate at which the woman's heart is beating;
a first numerical display member for numerically displaying the woman's heartbeat rate;
a second sensor circuit including an audio sensor for detecting the heartbeat of the fetus and generating a second electrical signal representative of that heartbeat;
an enabling circuit having a first input connected to said first sensor circuit, a second input connected to said second sensor circuit, and an output, said enabling circuit responsive to the first electrical signal and the second electrical signal for generating an enabling signal on said enabling circuit output during presence of the woman's heartbeat when the rate of the detected fetal heartbeat exceeds the rate of the detected woman's heartbeat by at least a preset amount;
a second display device including a third substantially solid red, heart-shaped display member for generating a visual display of a third heart and a fourth substantially solid red, heart-shaped display of a fourth heart within the third heart, said second display device connected to said enabling circuit and to said second sensor and responsive to second electrical signal during presence of the enabling signal for alternately energizing said third heart-shaped display member and said fourth heart-shaped display member at a rate substantially equal to the rate of the fetal heartbeat to represent a heart contracting at the rate at which the fetal heart is beating;

a second numerical display member for numerically displaying the fetal heartbeat rate;

a first alarm signal circuit connected to sid first sensor for generating a first alarm signal when the detected fetal heartbeat is at an abnormal rate;

a second alarm signal circuit connected to said second sensor for generating a second alarm signal when the detected fetal heartbeat is at an abnormal rate;

a third sensor circuit including a pressure sensor device for detecting movement of the fetus and generating a third electrical signal representative of the movement;

a third display device connected to said enabling circuit output and to said third sensor circuit and responsive to the third electrical signal during the presence of the enabling signal for depicting a representation of the fetal movement;

a third numerical display member connected to said enabling circuit output and to said third sensor circuit and responsive to the third electrical signal during the presence of the enabling signal for numerically displaying the intensity of the fetal movement;

a fourth numerical display member connected to said enabling circuit output and to said third sensor circuit and responsive to the third electrical signal during the presence of the enabling signal for numerically displaying the frequency of the fetal movement;

means for determining the rate of change of the fetal heartbeat rate;

means for inhibiting said third display device, said third numerical display member, said fourth numerical display member when the rate of change of the fetal heartbeat rate is less than a predetermined amount;

a microphone;

a speaker coupled to said microphone for providing audio signals corresponding with sounds detected by said microphone;

means positioning said speaker adjacent said second sensor circuit to permit providing of audi stimulation to the fetus and detecting effects of such audio stimulation on the detected fetal heartbeat and movement;

means for recording signals indicative of the fetal heartbeat and movement and of the woman's heartbeat; and means for playing back the recorded fetal heartbeat and movement signals and the recorded woman's heartbeat signals.

35. An obstetrical device for monitoring and displaying a representation of the heartbeats of a pregnant woman and her fetus, said device comprising:

a housing;

a first sensor circuit in said housing for detecting the heartbeat of the pregnant woman and generating a first electrical signal representative of that heartbeat;

first display means in said housing connected to said first sensor circuit and responsive to the first electrical signal for providing a first visual signal representative of the pregnant woman's heartbeat;

a second sensor circuit in said housing for detecting the heartbeat of the fetus and generating a second electrical signal representative of that heartbeat; and second display means in said housing connected to said second sensor circuit and responsive to the second electrical signal for providing a second visual signal representative of the fetal heartbeat.

36. An obstetrical device for providing audio stimuli to a fetus and monitoring and displaying a representation of fetal response to said stimuli, comprising:

a housing;

a microphone connected to said housing;

a speaker, operably connected for transmitting audio stimuli from said microphone, disposed adjacent a lower portion of said housing adapted for abutment with a mother's abdomen; and a sensor circuit in said housing for monitoring fetal response to said audio stimuli.

37. A device as claimed in claim 36, wherein said sensor circuit comprises means for detecting movement of the fetus and for generating an electrical signal representative of the movement; and display means connected to said sensor circuit and responsive to the electrical signal for providing a visual signal representative of the fetal movement.

38. A device as claimed in claim 36, wherein said sensor circuit comprises means for detecting fetal heartbeat and for generating electrical signal representative of the heartbeat; and display means connected to said sensor circuit and responsive to the electrical signal for providing a visual signal representative of the fetal heartbeat.

39. A device as claimed in claim 1, further comprising manual override switching means for activating said second display means in the absence of said enabling signal.

* * * * *

UNITED STATES PATENT AND TRADEMARK OFFICE
CERTIFICATE OF CORRECTION

PATENT NO. : 4,898,179

DATED : February 6, 1990

INVENTOR(S) : Vladimir Sirota

It is certified that error appears in the above-identified patent and that said Letters Patent is hereby corrected as shown below:

In the title of the invention, change

"MATERIAL" to --MATERNAL--.

Signed and Sealed this

Twelfth Day of March, 1991

Attest:

HARRY F. MANBECK, JR.

*Attesting Officer*  *Commissioner of Patents and Trademarks*